(12) United States Patent
Shimoyama

(10) Patent No.: US 9,452,071 B2
(45) Date of Patent: Sep. 27, 2016

(54) STENT DELIVERY SYSTEM

(71) Applicant: TERUMO KABUSHIKI KAISHA, Shibuya-ku (JP)

(72) Inventor: Masakazu Shimoyama, Kanagawa (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 574 days.

(21) Appl. No.: 13/947,560

(22) Filed: Jul. 22, 2013

(65) Prior Publication Data

US 2013/0304189 A1    Nov. 14, 2013

Related U.S. Application Data

(63) Continuation of application No. PCT/JP2012/050048, filed on Jan. 5, 2012.

(30) Foreign Application Priority Data

Mar. 3, 2011  (JP) ................. 2011-045791

(51) Int. Cl.
 A61F 2/966     (2013.01)
 A61F 2/07      (2013.01)
 A61F 2/95      (2013.01)

(52) U.S. Cl.
 CPC ............... *A61F 2/966* (2013.01); *A61F 2/07* (2013.01); *A61F 2002/9517* (2013.01)

(58) Field of Classification Search
 CPC .......... A61F 2/966; A61F 2/07; A61F 2/962; A61F 2002/9517; A61F 2002/9522; A61F 4/00
 See application file for complete search history.

(56) References Cited

U.S. PATENT DOCUMENTS 5,662,320 A  *  9/1997  Fujiwara  ................ B65H 1/266
                                                    271/3.14
8,708,210 B2   4/2014  Zemlok et al.
(Continued)

FOREIGN PATENT DOCUMENTS

JP        62-118226 U    7/1987
JP         3-51259 U     5/1991
(Continued)

OTHER PUBLICATIONS

International Search Report (PCT/ISA/210) issued on Apr. 17, 2012, by the Japanese Patent Office as the International Searching Authority for International Application No. PCT/JP2012/050048.
(Continued)

*Primary Examiner* — Jocelin Tanner
(74) *Attorney, Agent, or Firm* — Buchanan Ingersoll & Rooney PC

(57) ABSTRACT

A stent delivery system includes a housing that houses a rotary roller, a support body in sliding contact with the outer surface of the rotary roller, and a resilient member composed of a coil spring acting on the support body. If, for any reason, it becomes difficult to axially move a rack member and an operator forcibly rotates the rotary roller, a load of not less than a predetermined value is applied to the rotary roller and the rotary roller moves downward while the support body is being pushed down, and meshing engagement between the rack member and the rotary roller is released. Axial movement of the rack member is thus avoided as there is no transmission of the rotating force of the rotary roller to the rack member. Other embodiments are also disclosed for preventing transmission of the rotating force of the rotary roller to the rack member.

12 Claims, 11 Drawing Sheets

(56) References Cited

U.S. PATENT DOCUMENTS

| | | | |
|---|---|---|---|
| 2003/0028236 A1* | 2/2003 | Gillick | A61F 2/95 623/1.11 |
| 2003/0144671 A1* | 7/2003 | Brooks | A61F 2/95 606/108 |
| 2005/0060016 A1 | 3/2005 | Wu et al. | |

FOREIGN PATENT DOCUMENTS

| | | |
|---|---|---|
| JP | 2005-09113 A | 4/2005 |
| JP | 2007-504897 A | 3/2007 |
| JP | 2008-093437 A | 4/2008 |
| WO | WO 2005/032614 A2 | 4/2005 |

OTHER PUBLICATIONS

The extended European Search Report issued on Aug. 7, 2014, by the European Patent Office in corresponding European Patent Application No. 12752266.2-1662. (5 pages).

Office Action issued on Aug. 25, 2015, by the Japanese Patent Office in corresponding Japanese Patent Application No. 2013-502206. (4 pages).

* cited by examiner

STENT DELIVERY SYSTEM

CROSS REFERENCES TO RELATED APPLICATIONS

This application is a continuation of International Application No. PCT/JP2012/050048 filed on Jan. 5, 2012, and claims priority to Japanese Application No. 2011-045791 filed on Mar. 3, 2011, the entire content of both of which is incorporated herein by reference.

TECHNICAL FIELD

The present invention generally relates to a stent delivery system for delivering and indwelling a stent into a lumen of a living body such as a blood vessel.

BACKGROUND DISCUSSION

Conventionally, there have been cases where a stent which is formed from a metallic wire or the like in the shape of a hollow cylinder having a multiplicity of openings in its side wall and which is expandable in a lumen of a living body, such as a blood vessel, bile duct, trachea, esophagus and urethra, is used for improving a lesion part (stenosed part or obliterated part) in the lumen of the living body.

In the case of a self-expandable stent in which the stent itself has a self-expanding function, for example, there has been known a stent delivery system in which the stent is delivered into the living body in the state of being compressed and contained in a gap between an inner tube and an outer tube, and then the outer tube is retracted proximally so as to release the stent, whereby the stent is put indwelling (indwelled) in the lesion part.

As disclosed in Japanese Application Publication No. 2007-504897 (JP-T-2007-504897), for example, the above-mentioned stent delivery system has an operating mechanism for displacing the outer tube in an axial direction relative to the inner tube. In the operating mechanism, a gear rack is meshed with a gear of a rotatable wheel, and the outer tube is connected to an end portion of the gear rack. With the wheel rotated in a predetermined direction, the gear rack is advanced and retracted in the axial direction so as to move the outer tube relative to the inner tube, whereby the stent is released to the exterior of the outer tube.

In the stent delivery system having the operating mechanism as above-mentioned, however, the gear rack and the outer tube connected to the gear rack can be moved in the axial direction attendantly on the rotation of the wheel. Therefore, in the case where the outer tube is caught in the lesion part in a lumen of a living body or the like so that movement of the outer tube in the axial direction is made difficult, for example, if an operator continues to forcibly rotate the wheel, the gear rack and the outer tube are forcibly pulled in the axial direction. This is attended by exertion of an excessive load on the stent delivery system (especially, on the outer tube). As a result, the stent delivery system would be broken, so that a broken component part of the stent delivery system may be left in the lumen of the living body.

SUMMARY

According to one aspect, a stent delivery system comprises: an inner tube; a stent possessing a center axis, with the stent being compressed toward the center axis and being disposed on a distal-side outer surface of the inner tube during insertion of the stent into a lumen of a living body, and with the stent being restorable into its pre-compression shape by expanding outwardly when indwelled in the lumen of the living body; an outer tube disposed on an outer surface side of the inner tube and possessing a lumen containing the stent, wherein the outer tube permits release of the stent to exterior of the stent deliver system by axially and proximally moving the outer tube relative to the inner tube; and an operating unit for axially moving the outer tube relative to the inner tube. The operating unit includes: a housing; a rotary body rotatably supported relative to the housing so that the rotary body is rotatable relative to the housing, the rotary body possessing a first tooth portion; a rack body axially movable relative to the housing so that the rack body is movable relative to the housing in an axial direction, with the rack body possessing a second tooth portion in meshing engagement with the first tooth portion, and the rack body being connected to the outer tube so that the rack body and the outer tube move together in the axial direction; and a releasing mechanism by which the meshing engagement between the rotary body and the rack body is released when a load of not less than a predetermined value is exerted on either one of the rotary body and the rack body.

In the stent delivery system for putting a stent indwelling in a lesion part in a lumen of a living body, the operating unit by which the outer tube disposed on the outer surface side of the inner tube is moved in the axial direction includes: the housing; the rotary body supported so as to be rotatable relative to the housing and having the first tooth portion; and the rack body having the second tooth portion meshed with the first tooth portion, being movable in the axial direction relative to the housing, and being connected to the outer tube. The operating unit is provided with the releasing mechanism by which meshing between the rotary body and the rack body can be released when a load of not less than a predetermined value is exerted on either one of the rotary body and the rack body.

The stent delivery system is configured so that breakage due to exertion of an excessive load when movement of the outer tube becomes difficult can be prevented from occurring.

Even in the case where axial movement of the rack body and the outer tube connected to the rack body becomes difficult for some reason and the operator forcibly rotates the rotary body, the releasing mechanism ensures that when a load of not less than a predetermined value is exerted on the rotary body or the rack body, the meshed state of the first tooth portion of the rotary body and the second tooth portion of the rack body is released. In such a case, therefore, transmission of the rotating force of the rotary body to the rack body is prevented from occurring. Accordingly, a situation in which the rack body and the outer tube would be forcibly pulled in the axial direction is obviated. As a result, each component constituting the stent delivery system can be securely prevented from being broken due to exertion of an excessive load, so that a situation in which, for example, a broken part would be left in a living body lumen can be avoided.

According to another aspect, a stent delivery system comprises: an inner tube possessing a lumen and open opposite ends communicating with the lumen, with the inner tube possessing an outer surface; an outer tube possessing an inner surface and surrounding the inner tube so that a space exists between the inner surface of the outer tube and the outer surface of the inner tube, with the outer tube being axially movable relative to the inner tube; a stent positioned in the space between the inner surface of the outer tube and the outer surface of the inner tube, wherein the stent is compressed radially inwardly and disposed in surrounding relation to the inner tube, and is expandable radially outwardly to be indwelled in the lumen of the living body when the outer tube is axially moved relative to the inner tube to expose the stent to the exterior of the outer tube; and an operating unit for axially moving the outer tube relative to the inner tube. The operating unit comprises: a housing possessing an interior in which is positioned the inner tube and the outer tube; a rotary body rotatably supported on the housing so that the rotary body is manually rotatable relative to the housing, with the rotary body possessing an outwardly projecting first tooth portion; an axially movable second tooth portion in meshing engagement with the first tooth portion so that rotation of the rotary body results in axial movement of the second tooth portion, wherein the second tooth portion is connected to the outer tube so that axial movement of the second tooth portion resulting from rotation of the rotary body results in axial movement of the outer tube; and a resilient deformable member which is positioned in the housing in operative association with either the rotary body or the second tooth portion and which is deformed when a load of not less than a predetermined value is exerted on the rotary body so that the first tooth portion and the second tooth portion move out of meshing engagement with one another to prevent rotation of the rotary body from being transferred to the second tooth portion by way of the first tooth portion.

In accordance with another aspect, a method of operating a stent delivery system comprises: advancing an outer tube and an inner tube of a stent delivery system along a guide wire inside a lumen of a living body, wherein the inner tube is positioned inside the outer tube with a space between an inner surface of the outer tube and an outer surface of the inner tube, and wherein the stent delivery system also includes: a compressed stent positioned in the space between the inner surface of the outer tube and the outer surface of the inner tube; a housing in which at least a portion of the inner and outer tube are located; a rotary body rotatably supported relative to the housing and possessing a first tooth portion; and a rack body axially movable relative to the housing and possessing a second tooth portion in meshing engagement with the first tooth portion, with the rack body being connected to the outer tube so that the rack body and the outer tube move together in the axial direction. The method additionally involves stopping the advancing of the inner and outer tube within the lumen of the living body; rotating the rotary body so that the meshing engagement between the first tooth portion and the second tooth portion causes the rack body and the outer tube to move in a proximal direction relative to the inner tube to expose the stent so that the stent expands outwardly; and releasing the meshing engagement between the first tooth portion of the rotary body and the second tooth portion of the rack body when a load of not less than a predetermined value is exerted on either one of the rotary body and the rack body.

DETAILED DESCRIPTION

Figure 1:
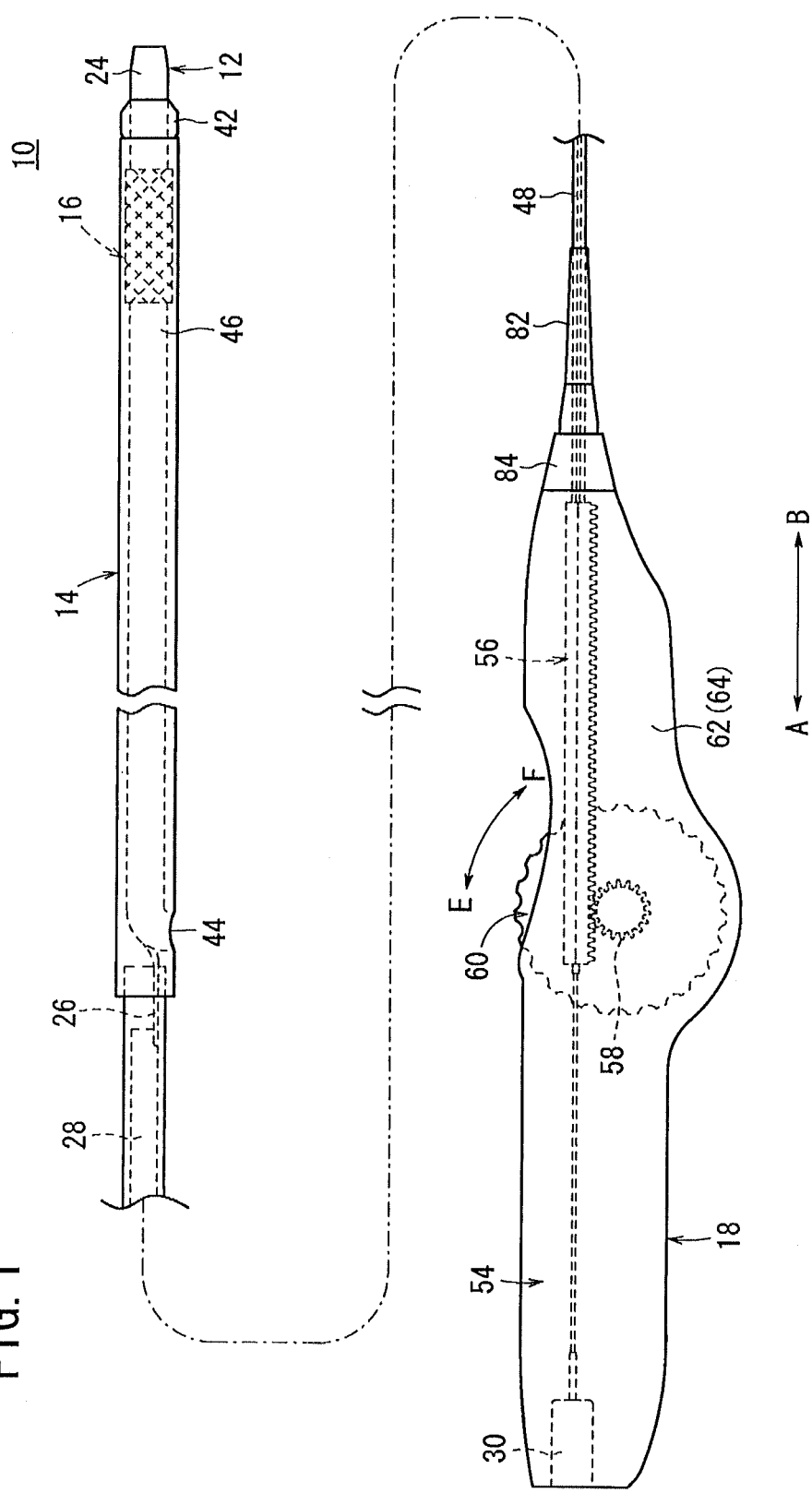
FIG. 1 is a side view of a stent delivery system according to one embodiment disclosed here.

Referring initially to FIG. 1, the stent delivery system 10 according to a first embodiment includes: an inner tube body (inner tube) 12 formed in or possessing a tubular shape; an outer tube body (outer tube) 14 disposed on the outer circumference side of the inner tube body 12 in surrounding relation to the inner tube 12; an expandable stent 16 located between the inner tube body 12 and the outer tube body 14; and an operating unit 18 which moves the outer tube body 14 in relation to the inner tube body 12.

In FIG. 1, the left side of the inner tube body 12 and the outer tube body 14 is referred to as the "proximal end (rear end)" side or proximal end (direction of arrow A), and the right side of the inner tube body 12 and the outer tube body 14 is referred to as the "distal end" side (direction of arrow B) or distal end. This same terminology applies to the other drawings figures.

Figure 2:
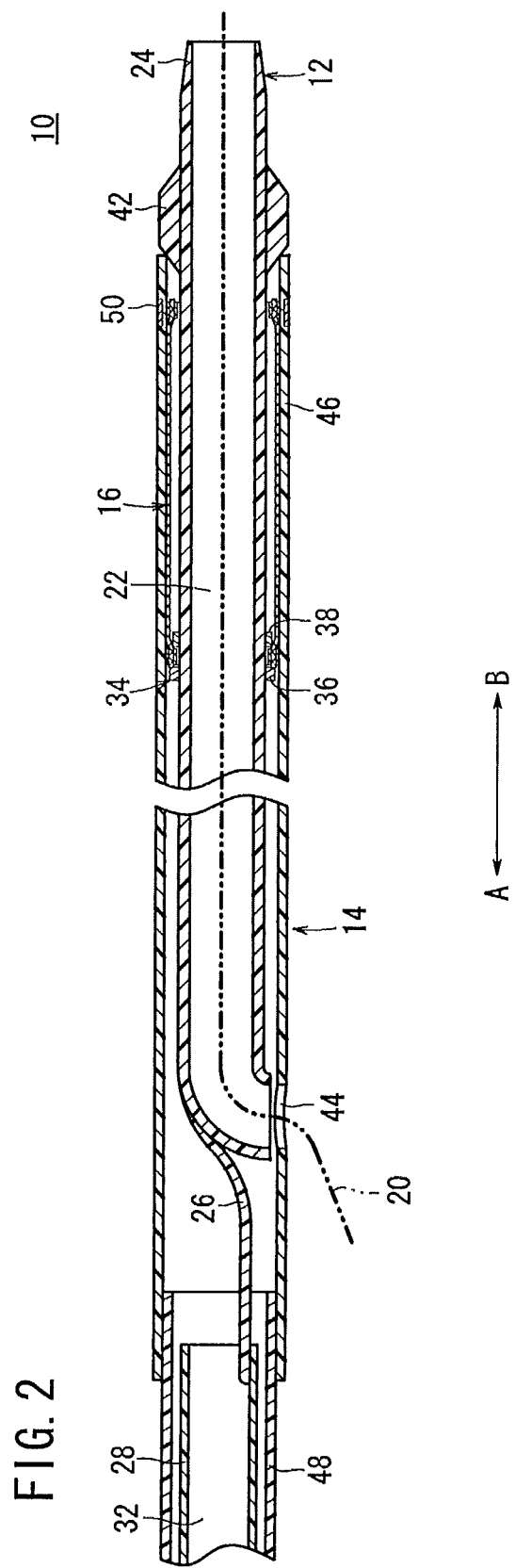
FIG. 2 is a longitudinal cross-sectional view of a portion of an inner tube body and an outer tube body of the stent delivery system shown in FIG. 1.
Figure 3:
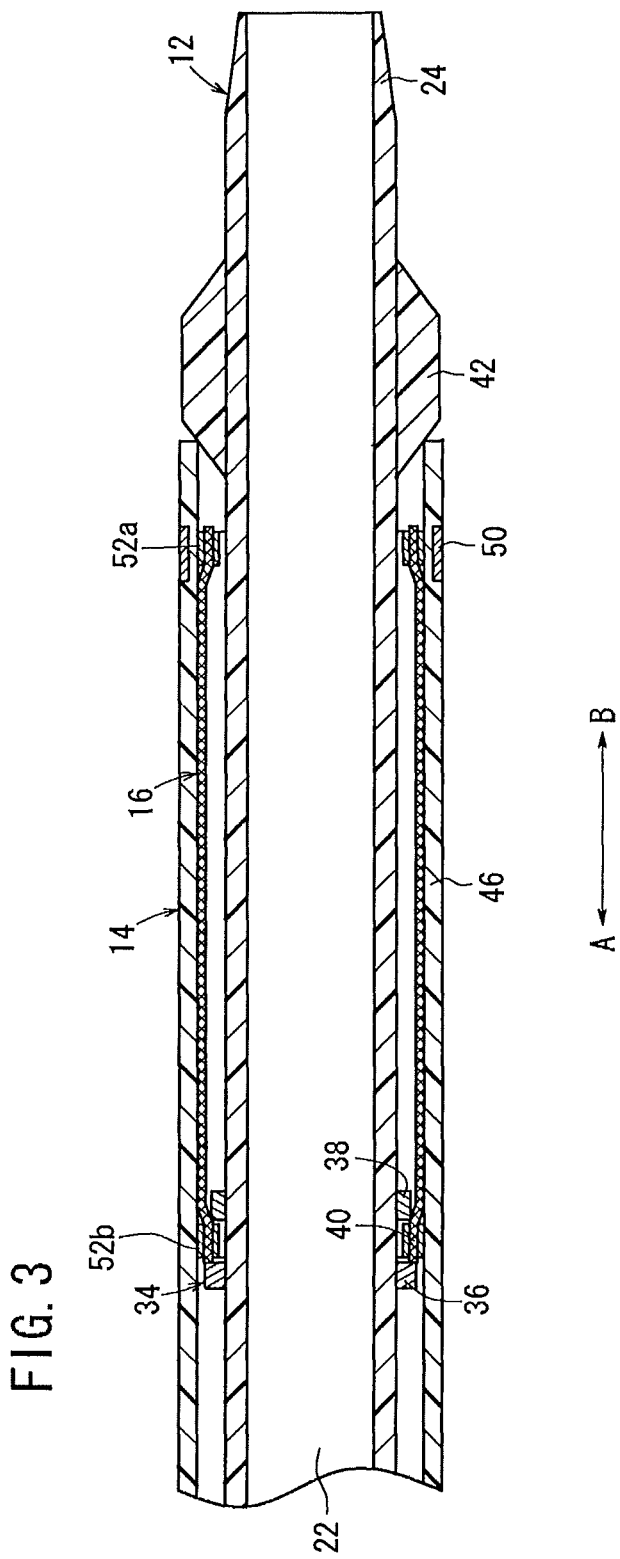
FIG. 3 is an enlarged longitudinal cross-sectional view of the distal end portions of the inner tube body and the outer tube body shown in FIG. 2.

As shown in FIGS. 1 to 3, the inner tube body 12 includes: a first distal tube 24 possessing a guide wire lumen 22 in which is inserted and passes a guide wire 20 (see FIG. 2); a first proximal tube 28 connected through a connecting member 26 to the proximal end portion (the direction of arrow A) of the first distal tube 24; and a connector 30 connected to the proximal end of the first proximal tube 28.

This inner tube body 12 is composed of tubular bodies, in which the distal ends and proximal ends of the first distal tube 24 and the first proximal tube 28 are open respectively, and the distal end of the first distal tube 24 is so disposed as to protrude distally beyond the distal end of the outer tube body 14. The above-mentioned guide wire 20 is used, for example, for guiding the stent delivery system 10 to a lesion part in a lumen of a living body.

The inner tube body 12 has a structure in which the proximal end of the first distal tube 24 and the distal end of the first proximal tube 28 are connected to each other, through the connecting member 26, inside the outer tube body 14. In addition, the first proximal tube 28 has a lumen 32 penetrating throughout from the distal end to the proximal end of the first proximal tube 28. A liquid such as physiological saline is injected via the connector 30 into the lumen 32. It is preferable that the first distal tube 24 is formed from a highly flexible resin material, and the first proximal tube 28 is formed from a high-strength metallic material. The first distal tube 24 and the first proximal tube 28 are thus preferably made of different materials.

The first distal tube 24 is provided with a stent holding mechanism 34 which functions at the time of re-containing the stent 16 after the stent 16 has been released to the exterior of the outer tube body 14 to an intermediate extent. As shown in FIG. 3, the stent holding mechanism 34 disposed on the outer circumferential surface of the inner tube body 12 includes a stent locking part 36 and a stent engaging part 38. The stent locking part 36 is disposed at a position located on the proximal side (the direction of arrow A) of the stent 16 (the proximal-most end of the stent 16) when the stent 16 is contained in the inside of the outer tube body 14. The stent engaging part 38 is disposed on the distal side (the direction of arrow B) of the first distal tube 24 relative to the stent locking part 36, and a reduced diameter section 40 of the stent 16 (to be described later) engages the stent engaging part 38.

The stent locking part 36 and the stent engaging part 38 are each annularly-shaped, they each protrude radially outwardly toward the outer tube body 14 side, and they are spaced apart from one another so that a predetermined spacing exists between the stent locking part 36 and the stent engaging part 38 along the axial direction of the first distal tube 24 (in the direction of arrows A and B). The height of the stent engaging part 38 is smaller than the height of the stent locking part 36. That is, the stent locking part 36 projects further radially outwardly than the stent engaging part 38.

This helps ensure that in a state in which the stent 16 is contained inside the outer tube body 14, the proximal end of the stent 16 makes contact with the stent locking part 36, and the reduced diameter section 40 of the stent 16 is retained between the stent locking part 36 and the stent engaging part 38, whereby the stent 16 is retained in such a position as not to be exposed to the exterior through the distal end of the outer tube body 14.

At the time when the stent 16 is released via the distal end of the outer tube body 14, the proximal end of the stent 16 contacts the stent locking part 36, whereby the stent 16 expands in the state of being positioned in a predetermined position. In addition, at the time when the stent 16 having been released to an intermediate extent is re-contained into the inside of the outer tube body 14, the reduced diameter section 40 makes contact with the stent engaging part 38, whereby the stent 16 is retained in the state of being positioned in a predetermined position.

A stopper part 42 is positioned at the distal end of the first distal tube 24. This stopper part 42 bulges radially outwardly and restricts distal movement of the outer tube body 14. This helps ensure that the outer tube body 14 is inhibited from protruding in the axial direction (in the direction of arrow B) relative to (distally beyond) the distal end of the inner tube body 12.

On the other hand, the proximal end of the first distal tube 24 is gently curved toward the radially outer side of the first distal tube 24, and communicates with and faces toward a guide wire leading-out hole 44 of the outer tube body 14.

Figure 4:
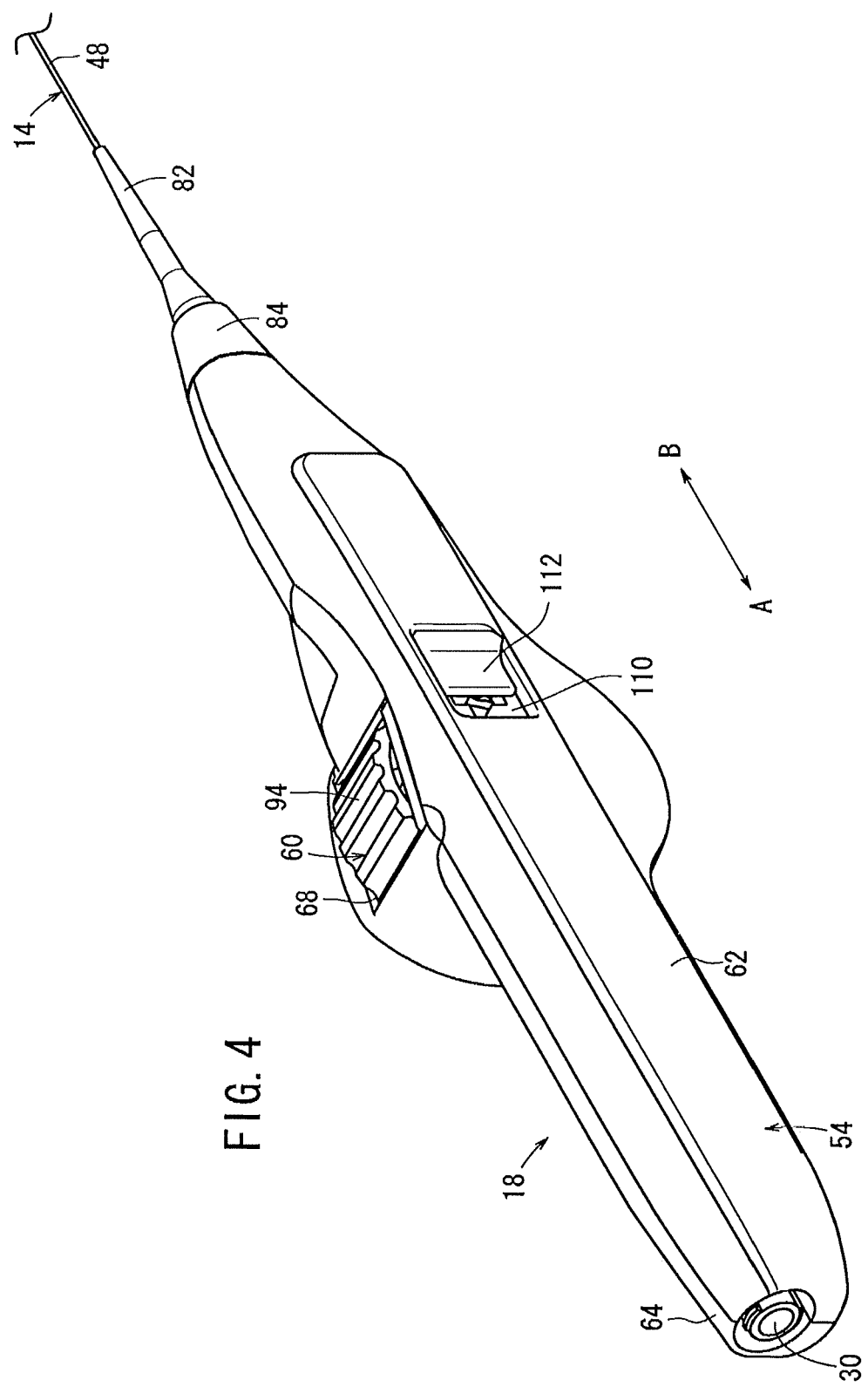
FIG. 4 is an external perspective view of an operating unit constituting the stent delivery system shown in FIG. 1.
Figure 5:
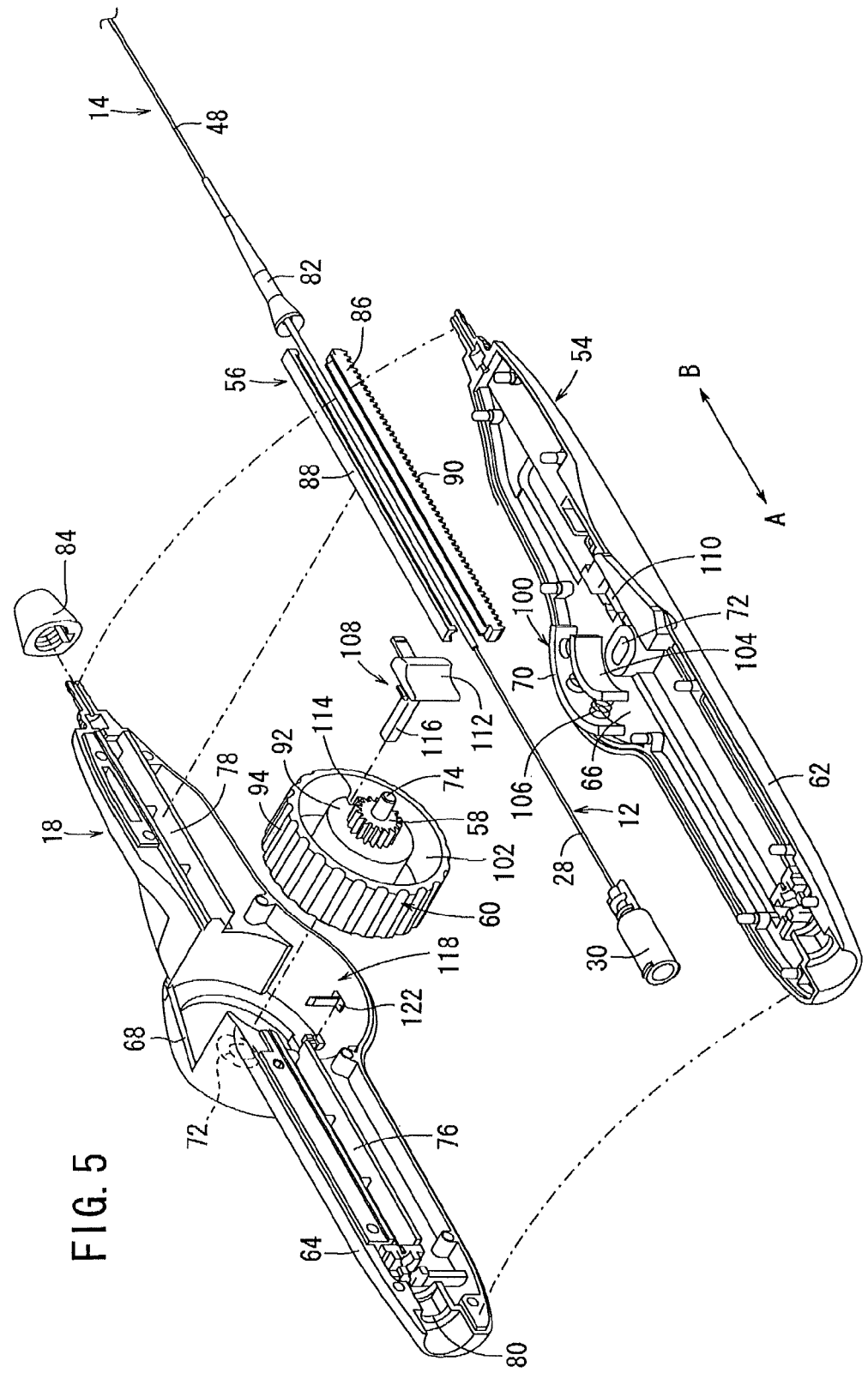
FIG. 5 is an exploded perspective view of the operating unit shown in FIG. 4.
Figure 6:
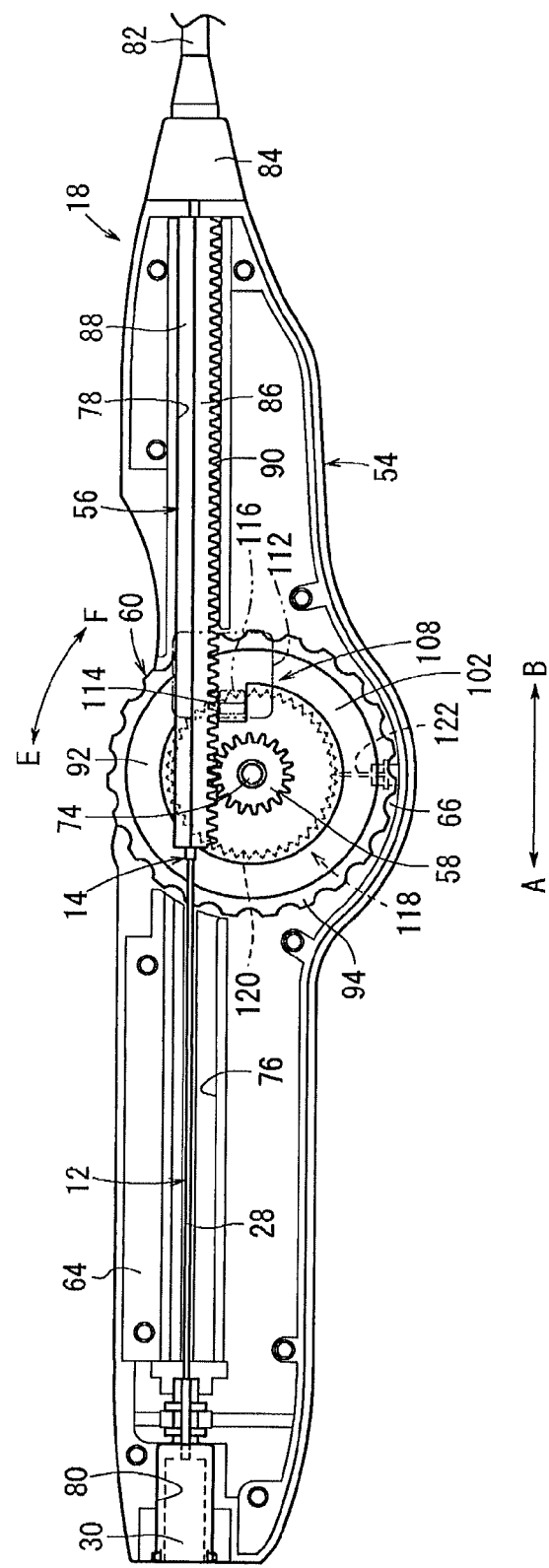
FIG. 6 is a side view of the inside of the operating unit shown in FIGS. 4 and 5.

As shown in FIGS. 4 to 6, the connector 30 possesses a hollow cylindrical shape, is connected to and communicates with the first proximal tube 28 of the inner tube body 12, and is so formed as to permit connection of the connector 30 to a liquid injector (e.g., syringe). In a state in which the liquid injector is connected to the connector 30, liquid is injected through the lumen 32 of the first proximal tube 28, and the liquid flows to the distal ends of the inner tube body 12 and the outer tube body 14, whereby the inside of the tube bodies can be flushed.

As shown in FIGS. 1 to 3, the outer tube body 14 is composed of tubular bodies. Specifically, the outer tube body 14 includes a second distal tube 46 in which the first distal tube 24 of the inner tube body 12 is disposed, and a second proximal tube 48 which is connected to the proximal side end (the direction of arrow A) or proximal end portion of the second distal tube 46 and in which the first proximal tube 28 is disposed. The distal end of the second distal tube 46 functions as a release port at the time of indwelling the stent 16 into a lesion part of a lumen of a living body, and functions also as a containing port at the time of containing the stent 16 having been released to an intermediate extent.

In addition, the guide wire leading-out hole 44 (though hole) is located on the proximal side (proximal end portion) of the second distal tube 46. The guide wire leading-out hole 44 opens to establish communication between the inner lumen of the second distal tube 46 and the exterior of the stent delivery device. The guide wire leading-out hole 44 is so provided that it can communicate with the opening of the guide wire lumen 22 of the first distal tube 24 provided inside the second distal tube 46. Through the guide wire leading-out hole 44, the guide wire 20 inserted and passed in the guide wire lumen 22 of the inner tube body 12 can be led out to the exterior of the stent delivery device.

Furthermore, at a distal portion of the second distal tube 46, a contrast marker 50 is disposed on the outer circumferential surface of the second distal tube 46. The contrast marker 50 is annular in shape and made of a radiopaque material, for example.

The stent 16 is formed in the shape of a substantially cylindrical mesh having a multiplicity of through openings. The stent 16 is a self-expandable stent which is disposed inside the second distal tube 46 of the outer tube body 14 in the state of being compressed radially inwardly (toward the center axis) at the time of insertion into a lumen of a living body, and which, by being released via the distal end of the outer tube body 14 into a lesion part in the lumen of the living body, can expand radially outward to be restored into its pre-compression shape. The material constituting the stent 16 is preferably a superelastic alloy such as Ni—Ti alloy, for example.

Contrast markers 52a and 52b are provided at the distal end and the proximal end of the stent 16. The contrast markers 52a and 52b each possess an annular shape and are made of a radiopaque material, for example. In addition, the reduced diameter section 40 of the stent 16, which is reduced radially inwardly, is provided at the proximal end of the stent 16. The reduced diameter section 40 is so formed as not to make contact with the outer circumferential surface of the inner tube body 12.

As shown in FIGS. 1 and 4 to 6, the operating unit 18 includes: a housing 54; a rack member (rack body) 56 contained inside the housing 54 and connected to the outer tube body 14; and a rotary roller 60 which has a first gear 58 meshing with the rack member 56 and by which the rack member 56 is displaced rectilinearly.

The housing 54 is round-shaped at its central portion, and is composed of a first housing 62 and a second housing 64 into which the housing 54 is bisected at the center in the thickness direction of the housing 54. The housing 54 is provided, inside the first and second housings 62 and 64, with a roller containing section 66 configured to contain the rotary roller 60 in a roughly central portion of the roller containing section 66. Part of the rotary roller 60 is exposed to the exterior through a roller hole 68 formed in the roller containing section 66 of the housing 54.

Figure 8A:
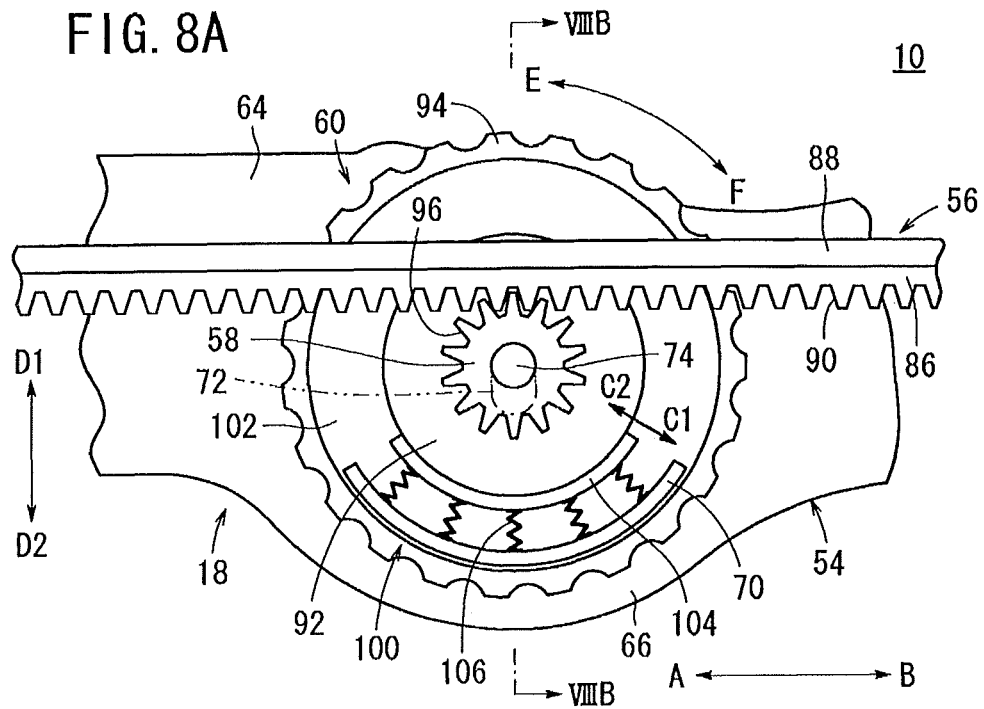
FIG. 8A is an enlarged side view of a portion of the stent delivery system in the vicinity of a rotary roller and a rack member shown in FIG. 6.
Figure 8B:
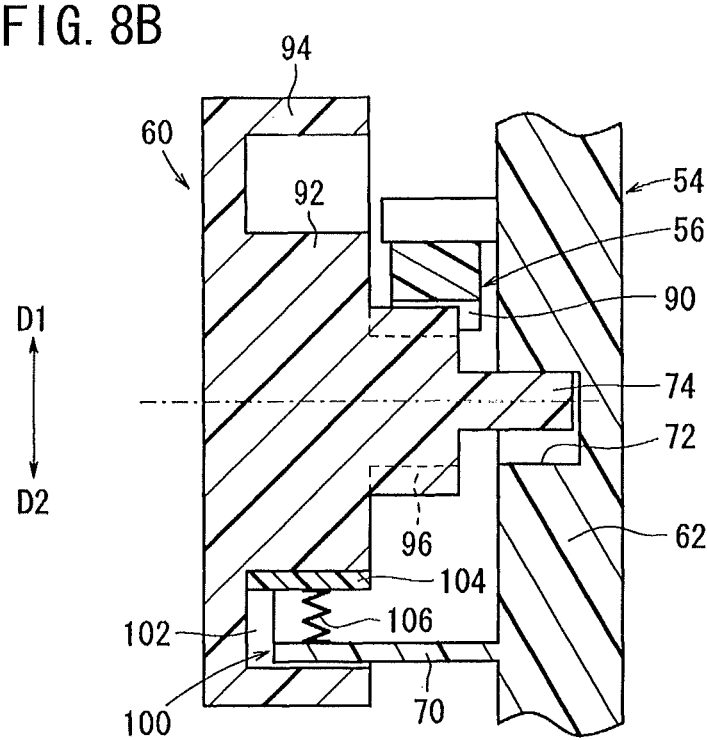
FIG. 8B is a cross-sectional view taken along the section line VIIIB-VIIIB in FIG. 8A.

As shown in FIGS. 5, 8 and 9, the roller containing section 66 is provided with a curved wall 70 projecting from an inner wall surface of the first housing 62 toward the second housing 64. The curved wall 70 possesses an arcuate cross-sectional shape curved toward the radially outer side (in the direction of arrow C1 in FIG. 8A) with the axis of the rotary roller 60 as a center (of a circle) and with a predetermined radius. The curved wall 70 is disposed downward relative to rotary shafts 74 of the rotary roller 60. The curved wall 70 extends over the range of a predetermined center angle about the rotary shafts 74. That is, the curved wall 70 extends over a limited circumferential extent as shown in FIG. 5.

In addition, the rotary roller 60 is rotatably supported by a pair of bearings 72 formed at inner wall surfaces of the first and second housings 62 and 64. The bearings 72 are recessed in relation to the inner wall surfaces of the first and second housings 62 and 64, and are formed in the shape of oblong holes which are elongated in the vertical direction (in the directions of arrows D1 and D2) orthogonal to the axial direction (the directions of arrows A and B) of the first and second housings 62 and 64. Thus, the rotary roller 60 is supported so as to be movable in the vertical direction (in the directions of arrows D1 and D2) through the rotary shafts 74 supported by the bearings 72.

First and second containing grooves 76 and 78 exist inside the second housing 64. The rack member 56 is contained and retained in the first and second containing grooves 76 and 78 so that the rack member 56 is movable in the axial direction (in the directions of arrows A and B). The first containing groove 76 is provided on the proximal end side (the direction of arrow A) in the second housing 64, while the second containing groove 78 is provided on the distal end side (the direction of arrow B) in the second housing 64. The roller containing section 66 is disposed between the first containing groove 76 and the second containing groove 78.

With the first housing 62 and the second housing 64 combined with each other, the rack member 56 is retained by the first and second containing grooves 76 and 78 in the state of being movable rectilinearly toward the distal side and the proximal end side.

A connector containing section 80 to contain the connector 30 is formed on the proximal end side (the direction of arrow A) relative to the first containing groove 76. The connector 30 is fixed to the housing 54 by being contained in the connector containing section 80. As a result, the proximal end of the first proximal tube 28 constituting the inner tube body 12 is fixed to the operating unit 18 through the connector 30.

The connector containing section 80 opens toward the proximal end side (in the direction of arrow A) of the housing 54, and is so formed that the liquid injector can be connected to the connector 30 from the exterior of the housing 54.

A distal nozzle 82 by which the second proximal tube 48 of the outer tube body 14 is slidably retained is mounted on the distal end of the housing 54. A through hole passes through the distal nozzle 82, and the second proximal tube 48 is positioned in the through hole and passes through the through hole. In the condition in which the distal nozzle 82 is mounted on the distal end of the housing 54, a cap 84 which surrounds the proximal end portion of the distal nozzle 82 is screw-engaged onto the distal end of the housing 54, whereby the distal nozzle 82 is fixed. In other words, the outer tube body 14, with the inner tube body 12 positioned in and passing inside the outer tube body 14 is inserted into the housing 54 through the distal nozzle 82, and is connected to the rack member 56.

The rack member 56 is composed of first and second blocks 86 and 88 which are straight and possess substantially symmetrical shapes. The proximal end portion of the second proximal tube 48 of the outer tube body 14 is fixed by being clamped between the first block 86 and the second block 88.

The rack member 56 composed of the first and second blocks 86 and 88 is positioned in the first and second containing grooves 76 and 78 inside the housing 54, whereby the rack member 56 is retained in the state of being rectilinearly movable toward the distal side and the proximal side of the housing 54.

The first block 86 is positioned inside the housing 54 so as to front on the rotary roller 60, and the side surface of the first block 86 fronting on the rotary roller 60 is provided with a plurality of first tooth portions 90 defined by projections and recesses arranged along the axial direction (the direction of arrows A and B).

The rotary roller 60 includes a main body 92 having the pair of rotary shafts 74, and an annular section 94 spaced radially outward from the main body 92 and exposed to the exterior through the roller hole 68. The main body 92 and the annular section 94 are approximately equal in width (i.e., the main body 92 and the annular section 94 possesses an approximately equal axial dimension). The main body 92 possesses a cylindrical shape, and is provided at its center with the pair of rotary shafts 74 projecting in mutually spaced (opposite) directions. The rotary shafts 74 are positioned in the bearings 72 of the first and second housings 62 and 64, respectively.

In addition, the first gear 58 having a plurality of second tooth portions 96 projecting in the radially outward direction, with the rotary shafts 74 as a center, is provided at a side surface of the main body 92, and meshes with the first tooth portions 90 of the rack member 56. With the rotary roller 60 rotated, the rack member 56 is moved rectilinearly along the first and second containing grooves 76 and 78.

The operating unit 18 is provided with a releasing mechanism 100 by which the meshing engagement between the rotary roller 60 and the rack member 56 is released in the situation where the outer tube body 14 comes to be unmovable relative to the inner tube body 12 and a load G of not less than a predetermined value is exerted on the rotary roller 60.

The releasing mechanism 100 includes: a support body 104 which is arcuate in cross-sectional shape and which is provided in a space 102 between the main body 92 and the annular section 94; and a resilient member 106 which is provided between the support body 104 and the curved wall 70 and which biases the support body 104 toward the main body 92. The curved wall 70 is also disposed inside the space 102.

The support body 104 is so disposed as to make sliding contact with the outer circumferential surface of the main body 92. For example, the support body 104 is so formed as to have an inside diameter approximately equal to the outside diameter of the main body 92 and to have a predetermined thickness. The support body 104 faces the curved wall 70 and is disposed coaxially with the curved wall 70 and the rotary roller 60.

The resilient member 106 is composed, for example, of a plurality of coil springs, which are arranged at intervals along the outer circumferential surface of the support body 104, and constantly bias the support body 104 toward the rotary roller 60, or radially inward (in the direction of arrow C2). In addition, the resilient force of the resilient member 106 is appropriately set so that the pressure with which the support body 104 is pressed toward the rotary roller 60 (in the direction of arrow C2) will be a predetermined pressure. The setting of the resilient force will be described later.

The support body 104 is so supported as to be freely movable toward and away from the curved wall 70 through the resilient member 106. For the resilient member 106, a leaf spring, a resin material, a rubber and the like may also be used in place of the coil springs.

As a result of this, the inner circumferential surface of the support body 104 is constantly making sliding contact with the outer circumferential surface of the main body 92 under resiliency of the resilient member 106, thereby pressing the main body 92 radially inward (in the direction of arrow C2). As shown in FIG. 8A, therefore, the rotary roller 60 is rotatably retained in the condition in which the rotary shafts 74 are located upward (the direction of arrow D1) inside the bearings 72. In addition, the first gear 58 (the rotary roller 60) is biased toward the rack member 56, and the rotary roller 60 and the rack member 56 are in a meshed state.

In the above-mentioned operating unit 18, for example, the operator rotates the annular section 94 of the rotary roller 60 in a predetermined direction (in the direction of arrow E) relative to the housing 54, as shown in FIG. 6. By this operation, the rack member 56 inside the housing 54 is moved along the first and second containing grooves 76 and 78 toward the connector 30 (in the direction of arrow A), accompanied by movement (retraction) of the outer tube body 14 toward the proximal side of the housing 54. As a result, the stent 16 is released via the distal end of the outer tube body 14.

On the other hand, when the rotary roller 60 is rotated in the opposite direction to the above-mentioned (in the direction of arrow F) after the stent 16 is released to an intermediate extent, the rack member 56 is moved along the first and second containing grooves 76 and 78 in the direction for spacing away from the connector 30 (in the direction of arrow B). This is accompanied by movement (advancement) of the outer tube body 14 toward the distal side relative to the inner tube body 12, whereby the stent 16 is re-contained into the inside of the outer tube body 14.

As shown in FIG. 6, the operating unit 18 is provided with a locking mechanism 108 by which a moving motion of the rack member 56 can be restricted through restriction of a rotating motion of the rotary roller 60.

The locking mechanism 108 includes: a slide member 112 which is provided at a hole part 110 opening in a side surface of the first housing 62 so that it can be displaced by sliding (manual sliding); and a pin groove 114 formed in a side surface of the main body 92 of the rotary roller 60 so as to front on the slide member 112. The slide member 112 is so retained as to be rectilinearly displaceable toward the distal and proximal end sides (in the directions of arrows A and B) of the first housing 62 through the hole part 110.

When a pin 116 rectangular in cross-sectional shape projecting into the inside of the first housing 62 is inserted into the pin groove 114 of the rotary roller 60, in the condition where the slide member 112 is located on the proximal side of the housing 54, a rotating motion of the rotary roller 60 is restricted.

Therefore, the rack member 56 is prevented from moving in the axial direction, and, attendantly, a forward or backward movement of the outer tube body 14 is restricted.

In addition, with the slide member 112 moved toward the distal side of the housing 54 (in the direction of arrow B), the pin 116 is moved towards the radially outer side of the rotary roller 60 and is disengaged from the pin groove 114. Therefore, the restriction of rotation of the rotary roller 60 by the pin 116 is removed, resulting in a state in which the rack member 56 can be moved in the axial direction (in the directions of arrows A and B) under the rotating action of the rotary roller 60.

Furthermore, the operating unit 18 is provided with an intermittent mechanism 118 for putting the rotary roller 60 into intermittent rotation. The intermittent mechanism 118 includes: a second gear 120 disposed at a side surface, opposite to the first gear 58, of the rotary roller 60; and a notch member 122 retained by the second housing 64 and engaged with a tooth portion of the second gear 120. The notch member 122 is formed in the shape of an elastically deformable thin sheet, for example. The notch member 122 extends from a part retained by the second housing 64 toward the center of the second gear 120, and is engaged with the tooth portion of the second gear 120.

When the rotary roller 60 is rotated, the notch member 122 engaged with the second gear 120 is elastically deformed, disengages from a recess of the tooth portion and moves over a projection adjacent to the recess, thereby engaging another (adjacent) recess. This enables an intermittent rotating motion. Furthermore, the sound generated at the moment of engagement between the notch member 122 and the second gear 120 makes it possible to confirm the rotating motion and/or a rotational angle of the rotary roller 60.

The stent delivery system 10 of the first embodiment disclosed by way of example is configured as above-described. Set forth next is a description of the operation and effect of the stent delivery system 10. The following description assumes a state in which the guide wire 20 is inserted in a lumen of a living body (for example, a blood vessel), and its distal end has preliminarily been put indwelling (indwelled) in a lesion part in the lumen of the living body.

In such a preparatory state, flushing of the stent delivery system 10 shown in FIG. 1 is conducted. First, the operator connects a liquid injector to the connector 30 disposed at the proximal end of the operating unit 18, and injects a liquid from the liquid injector into the connector 30. As a result, the liquid flows to the distal end side of the inner tube body 12 and the outer tube body 14 (in the direction of arrow B). Then, the liquid having reached the distal end is ejected from the distal ends of the inner tube body 12 and the outer tube body 14, whereby flushing of the inside of the inner tube body 12 and the outer tube body 14 is completed exterior of a living body.

Next, as shown in FIG. 2, the proximal end of the guide wire 20 exposed to the exterior of the living body is inserted into the distal end of the inner tube body 12 and is passed or fed into the guide wire lumen 22, and the inner tube body 12 and the outer tube body 14 are gradually advanced along the guide wire 20 into the lumen of the living body. The proximal end of the guide wire 20 is led out to the exterior of the outer tube body 14 through the guide wire leading-out hole 44.

After the arrival of the distal end of the outer tube body 14 in the lesion part is confirmed by the contrast marker 50, the slide member 112 of the operating unit 18 is moved toward the distal side (in the direction of arrow B), and the pin 116 is disengaged from the pin groove 114 of the rotary roller 60, whereby the restriction imposed on rotation of the rotary roller 60 is removed. Then, the rotary roller 60 is rotated in a predetermined direction (in the direction of arrow E).

Figure 7:
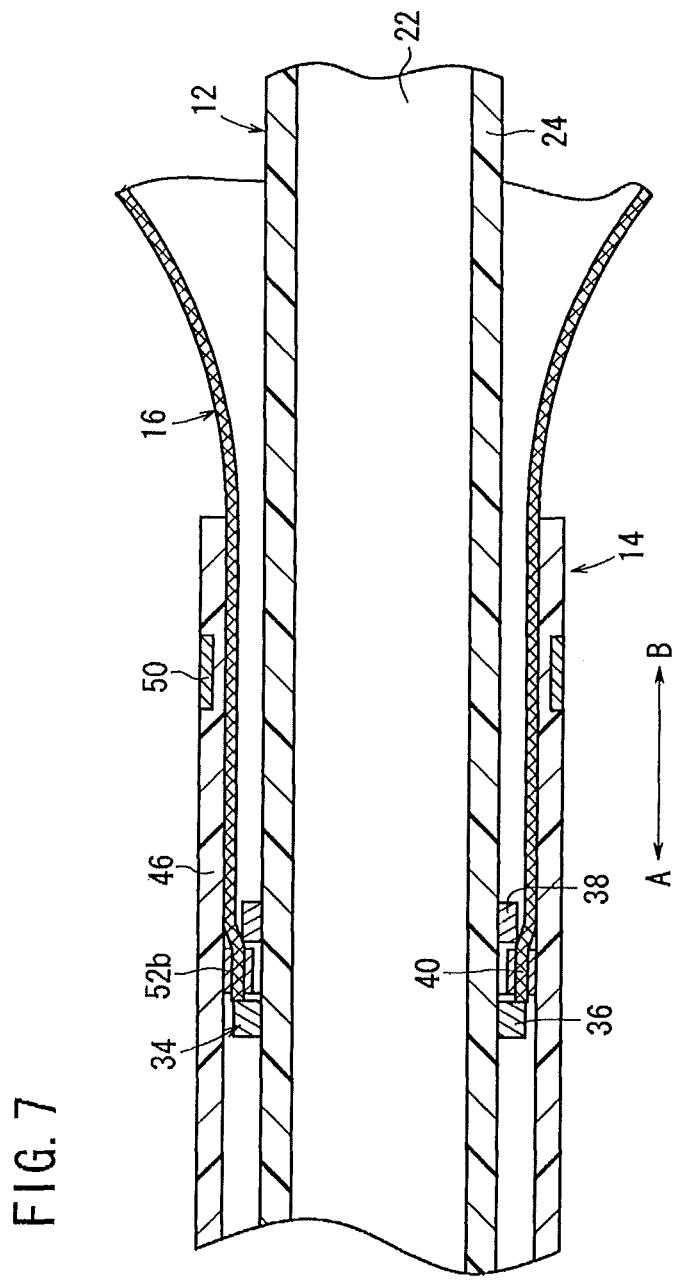
FIG. 7 is an enlarged longitudinal cross-sectional view of a portion of the stent delivery system showing a state in which a stent is released from the distal end of the outer tube body to an intermediate extent, or a case in which the stent released to an intermediate extent is contained into the inside of the outer tube body.

The rotation of the first gear 58 causes the rack member 56 to move in the proximal direction (in the direction of arrow A) within the housing 54. This is accompanied by gradual movement of the outer tube body 14 toward the proximal side of the operating unit 18. As a result, as shown in FIG. 7, the stent 16 contained in the outer tube body 14 starts being gradually exposed, starting from its distal portion; simultaneously, the stent 16 starts expanding (automatically expanding) radially outwardly. Then, the stent 16 comes into the state of being completely exposed from the outer tube body 14, whereby the stent 16 is put indwelling (indwelled) in the lesion part in the state of being expanded so that the stent 16 possesses the cylindrical shape.

At the time of releasing the stent 16 in the above-mentioned manner, for example, the rotary roller 60 of the operating unit 18 is rotated so as to gradually move the outer tube body 14 toward the proximal side or in the proximal direction (in the direction of arrow A). In this case, for example, the outer tube body 14 may be caught at (i.e., may catch on) the lesion part in the lumen of the living body, making it difficult to move the outer tube body 14 proximally. In such a situation, if the operator continues to forcibly rotate the rotary roller 60 in a predetermined direction, a load G of not less than a predetermined value would be exerted on the rotary roller 60 (the first gear 58) in the radially outward direction (in the direction of arrow C1) and in the vertically downward direction (in the direction of arrow D2), since it is difficult for the rack member 56 connected to the outer tube body 14 to move proximally (in the direction of arrow A).

Figure 9A:
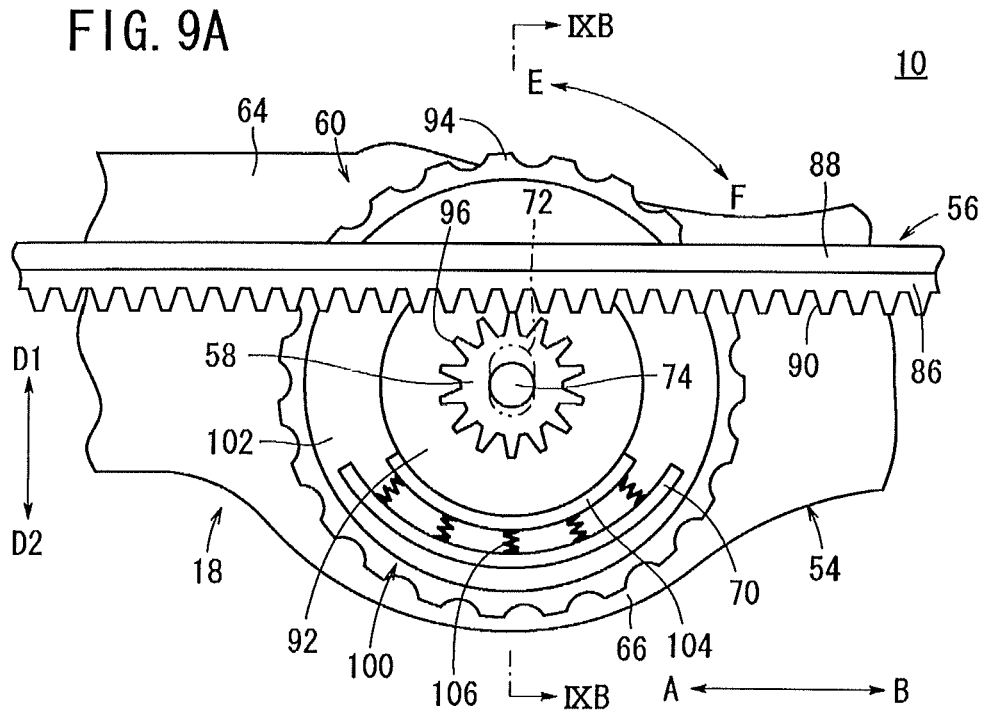
FIG. 9A is an enlarged side view of the portion of the stent delivery system depicted in FIG. 8A showing a non-meshed state in which the rotary roller shown in FIG. 8 goes down in a direction for being spaced away from the rack member.
Figure 9B:
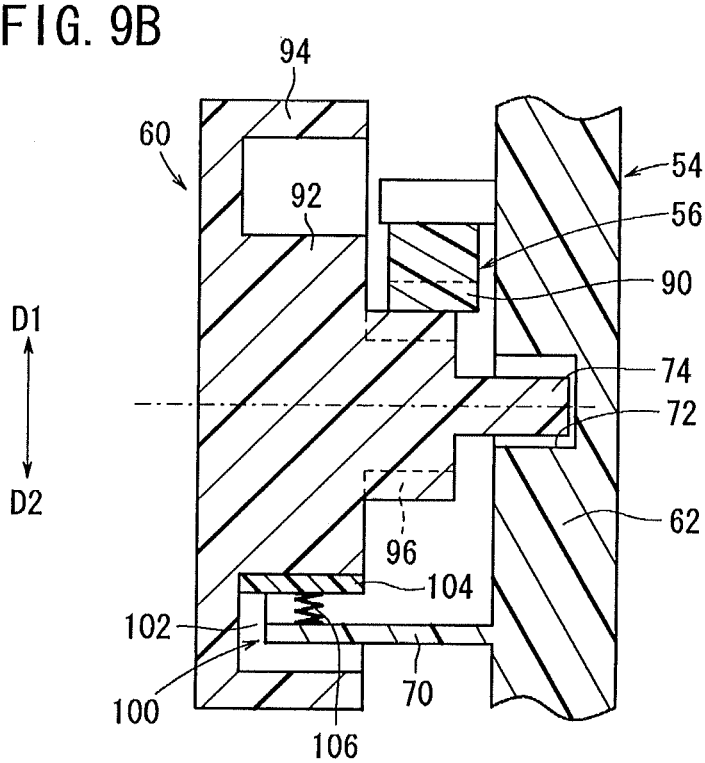
FIG. 9B is a cross-sectional view taken along the section line IXB-IXB in FIG. 9A.

Then, as shown in FIGS. 9A and 9B, the load G exerted on the rotary roller 60 causes the second tooth portion 96 of the first gear 58 to run onto the first tooth portion 90 of the rack member 56, and the rotary roller 60 is pressed down radially outward (in the direction of arrow C1) while compressing the resilient member 106 through the support body 104. That is, the load G exerted on the rotary roller 60 causes the second tooth portion 96 of the first gear 58 to become separated from or move out of meshing engagement with the first tooth portion 90 of the rack member 56. In this instance, the rotary roller 60 is moved by a predetermined distance in the vertically downward direction (in the direction of arrow D2) along the bearings 72 in which the rotary shafts 74 are positioned. Consequently, the first gear 58 of the rotary roller 60 and the first tooth portion 90 of the rack member 56 are put into a non-meshed state, so that transmission of the rotating force of the rotary roller 60 to the rack member 56 is avoided or does not occur.

As a result, even if the rotary roller 60 is rotated, the rack member 56 in the non-meshed state is not moved proximally, so that the rack member 56 and the outer tube body 14 of which movement has become difficult due to the catching or the like can be securely prevented from being forcibly pulled proximally. Accordingly, damage to the stent delivery system 10 which might be caused by forcible movement of the outer tube body 14 and the rack member 56 can be rather reliably avoided.

Specifically, when a load G of not less than a predetermined value is exerted on the rotary roller 60 in the radially outward direction (in the direction of arrow C1) and in the vertically downward direction (in the direction of arrow D2) in the state in which axial movement of the rack member 56 is restricted, the second tooth portion 96 of the rotary roller 60 comes over the first tooth portion 90 of the rack member 56 (i.e., the second tooth portion 96 separates from or moves out of meshing engagement with the first tooth portion 90), and the rotary roller 60 is moved radially outward against the resilience of the resilient member 106, to be put into a non-meshed state, namely, the state of being out of meshing engagement and contact with the rack member 56. The load G is appropriately set according to the resilient force of the resilient member 106. In addition, the load G is set on the basis of a lowest-yield-point part of such components as the outer tube body 14, the inner tube body 12, the operating unit 18, etc. constituting the stent delivery system 10.

Specifically, the load G is set on the basis of the lowest yield point of the components of the stent delivery system 10, and the resilient member 106 having a resilient force approximately equal to or lower than the load G is disposed between the curved wall 70 and the support body 104, thereby biasing the rotary roller 60 upward (toward the rack member 56 side). This helps ensure that when the load G is applied to the rotary roller 60, the rotary roller 60 is so moved as to be separated from the rack member 56, so that the meshing engagement between the rotary roller 60 and the rack member 56 is released, and exertion of a further load on the rack member 56 is avoided. Therefore, the lowest-yield-point component in the stent delivery system 10 is prevented from being plastically deformed beyond its yield point, and breakage of the component is securely prevented.

As above-described, in the first embodiment, the releasing mechanism 100 is provided by which meshing between the rotary roller 60 and the rack member 56 constituting the operating unit 18 can be released. This helps ensure that, even in the case where axial movement of the rack member 56 and the outer tube body 14 connected to the rack member 56 becomes difficult for some reason, when a load G of not less than a predetermined value is exerted on the rotary roller 60, the rotary roller 60 can move or shift down in the direction for being spaced from the rack member 56, and thereby to put the rotary roller 60 and the rack member 56 into a non-meshed state. The resilient member 106 is a resilient deformable member that allows the meshing engagement between the teeth 96 on the rotary roller 60 (gear 58) and the teeth 90 on the rack member 56 to be released when a load G of not less than a predetermined value is exerted on the rotary roller 60 as described above.

As a result, even in the case where the operator continues to forcibly rotate the rotary roller 60, the rack member 56 is prevented from being forcibly pulled due to rotation of the rotary roller 60. Therefore, breakage of the lowest-yield-point component in the stent delivery system 10 can be securely prevented. Accordingly, a situation in which, for example, a broken component is left in a lumen of a living body can be avoided.

Now, a stent delivery system 150 according to a second embodiment disclosed here will be described with reference to FIGS. 10A and 10B. Components in this second embodiment of the stent delivery system 150 that are the same as in the first embodiment of the stent delivery system 10 are designated by common reference numbers and a detailed description of such components is not repeated.

The stent delivery system 150 of the second embodiment differs from the stent delivery system 10 of the first embodiment in that a rack member 154 constituting an operating unit 152 is hollow and a first block 156 meshing with the first gear 58 is freely bendable.

Figure 10A:
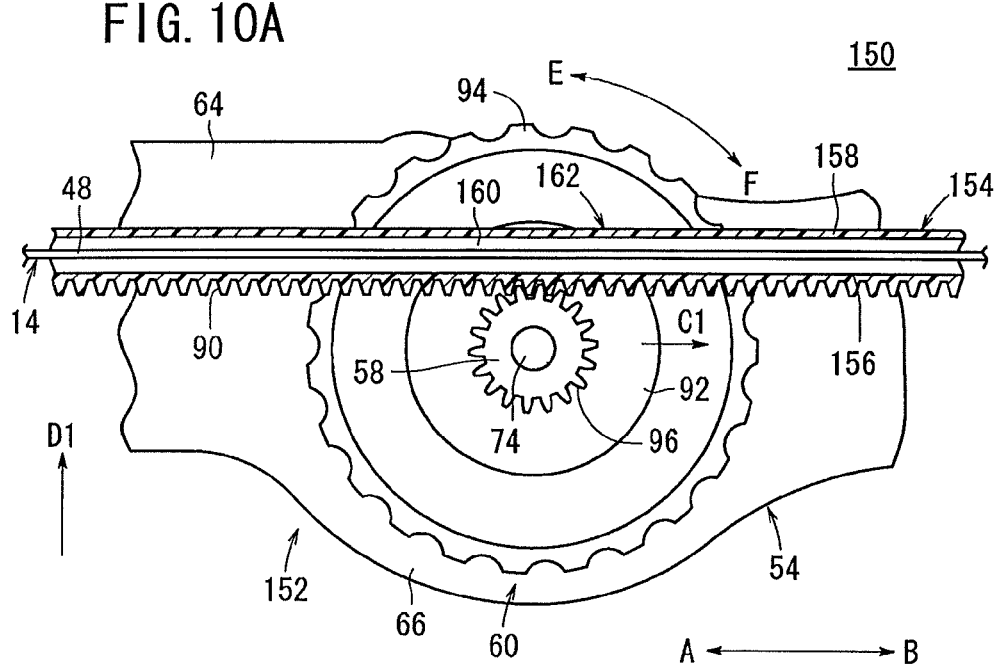
FIG. 10A is an enlarged side view of a portion of the stent delivery system in the vicinity of a rotary roller and a rack member in an operating unit of a stent delivery system according to another embodiment disclosed here.
Figure 10B:
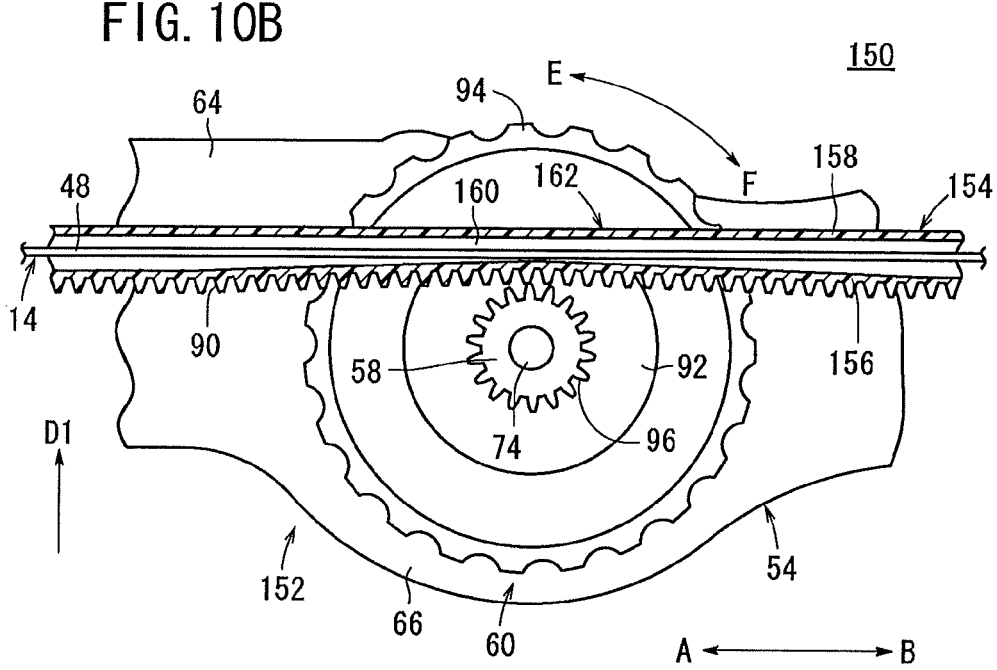
FIG. 10B is another enlarged side view showing a non-meshed state in which the rack member of FIG. 10A is bent upward and spaced from a first gear.

As shown in FIGS. 10A and 10B, the rack member 154 is configured to include first and second blocks 156 and 158 in which is formed an inner cavity 160, and the inner cavity 160 extends in the axial direction of the rack member 154 while having a substantially constant height. The height of the inner cavity refers to, as seen with reference to FIGS. 10A and 10B, the up and down dimension of the inner cavity 160 in the direction parallel to the arrow D1 direction. The first block 156 is freely bendable in a direction in which the first tooth portion 90 is spaced away from the first gear 58 of the rotary roller 60. More specifically, the first block 156 is so formed that its bottom surface having the first tooth portion 90 is freely bendable upward (in the direction of arrow D1) through the inner cavity 160 or by virtue of the inner cavity 160.

In the stent delivery system 150 having the rack member 154 as above-described, in the case where movement of the outer tube body 14 and the rack member 154 in the axial direction (in the directions of arrows A and B) becomes difficult for some reason and the operator continues to forcibly rotate the rotary roller 60, a load G of not less than a predetermined value is exerted on the rotary roller 60 radially outward (in the direction of arrow C1) and upward (in the direction of arrow D1) due to the rotation of the rotary roller 60, as shown in FIG. 10B.

In this second embodiment, also, the load G is set on the basis of a lowest-yield-point component of such components as the outer tube body 14, the inner tube body 12, the operating unit 152, etc. constituting the stent delivery system 150. Then, the second tooth portion 96 of the first gear 58 runs onto the first tooth portion 90 of the rack member 154 of which movement is restricted, and the first block 156 of the rack member 154 is deformed so as to be bent toward the second block 158 (in the direction of arrow D1).

More specifically, the first block 156 is elastically deformed upward so as to become arcuate in longitudinal cross-sectional shape, with its part meshed with the first gear 58 as a center, and comes into or moves into the inner cavity 160. This deformation of the first block 156 results in a non-meshed state in which meshing between the first gear 58 and the rack member 154 is released, so that transmission of the rotating force of the rotary roller 60 to the rack member 154 no longer occurs.

As a result, even if the rotary roller 60 is rotated, for example, the rack member 154 in the non-meshed state does not move proximally (in the direction of arrow A). Therefore, the outer tube body 14 and the rack member 154, movement of which in the axial direction has become difficult for some reason, can be securely prevented from being forcibly pulled in the axial direction. Accordingly, damage to the stent delivery system 150 which might be caused by forcible movement of the outer tube body 14 and the rack member 154 can be avoided relatively assuredly.

The first block 156 constituting the rack member 154 may be so configured that it is plastically deformed when the second tooth portion 96 of the first gear 58 runs onto the first tooth portion 90 and when it is bent upward (in the direction of arrow D1). That is, first block 156 may be configured to plastically deform when the second tooth portion 96 becomes separated from or moves out of meshing engagement with the first tooth portion 90. In this case, the first block 156 is retained in the state of being bent upward, so that its first tooth portion 90 is relatively perfectly prevented from meshing with the first gear 58. Consequently, the meshed state is prevented from being established again.

Thus, in the second embodiment, the rack member 154 provided with the inner cavity 160 functions as a releasing mechanism 162 by which the meshed state or meshing engagement of the rotary roller 60 and the rack member 154 constituting the operating unit 152 are released. The rack member 154 with the inner cavity 160 is thus a resilient deformable member that allows the meshing engagement between the teeth 96 on the rotary roller 60 (gear 58) and the teeth 90 on the rack member 154 to be released when a load G of not less than a predetermined value is exerted on the rotary roller 60 as described above.

As above-described, in the second embodiment, the rack member 154 constituting the releasing mechanism 162 is configured or constructed to be freely deformable in the direction for spacing away from the first gear 58 of the rotary roller 60 when a load G of not less than a predetermined value is exerted on the rotary roller 60 radially outward (in the direction of arrow C1) and upward (in the direction of arrow D1). This helps ensure that when such a load G is exerted, the first block 156 is bent in the direction for spacing away from the first gear 58 (in the direction of arrow D1), and the meshing engagement between the rotary roller 60 and the rack member 154 is released.

As a result, even in the case where the operator continues to forcibly rotate the rotary roller 60, the rack member 154 is prevented from being forcibly pulled due to the rotation of the rotary roller 60. Therefore, breakage of the lowest-yield-point component in the stent delivery system 150 can be relatively securely prevented. Accordingly, a situation in which a broken component of the stent delivery system 150 is left in a lumen of a living body can be avoided.

Now, a stent delivery system 200 according to a third embodiment disclosed here will be described with reference to FIGS. 11A and 11B. Components in this third embodiment of the stent delivery system 200 that are the same as in the first and second embodiments of the stent delivery system 10, 150 are designated by common reference numbers and a detailed description of such components is not repeated.

Figure 11A:
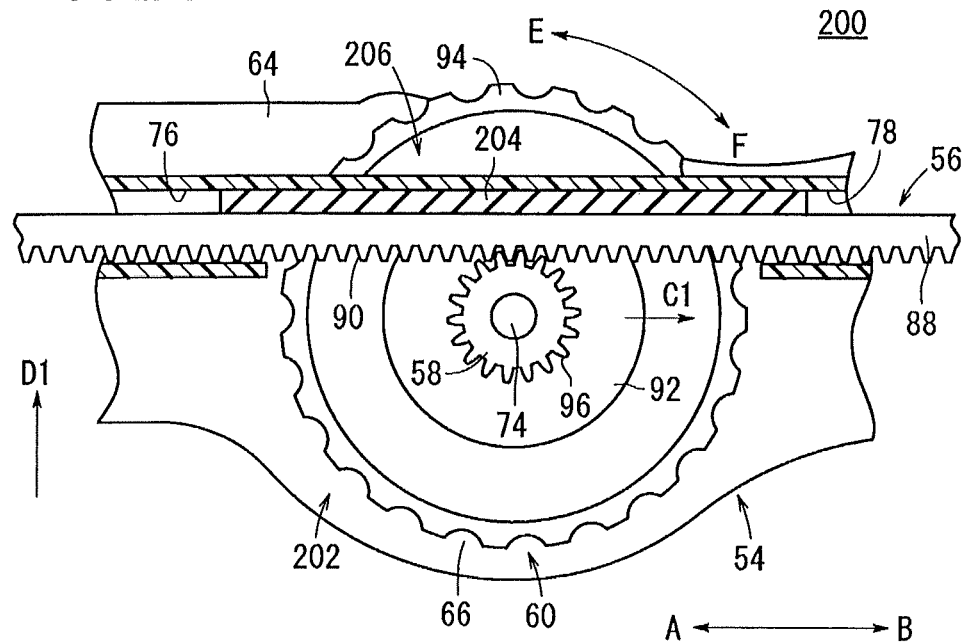
FIG. 11A is an enlarged side view of a portion of the stent delivery system in the vicinity of a rotary roller and a rack member in an operating unit of a stent delivery system according to a further embodiment disclosed here.
Figure 11B:
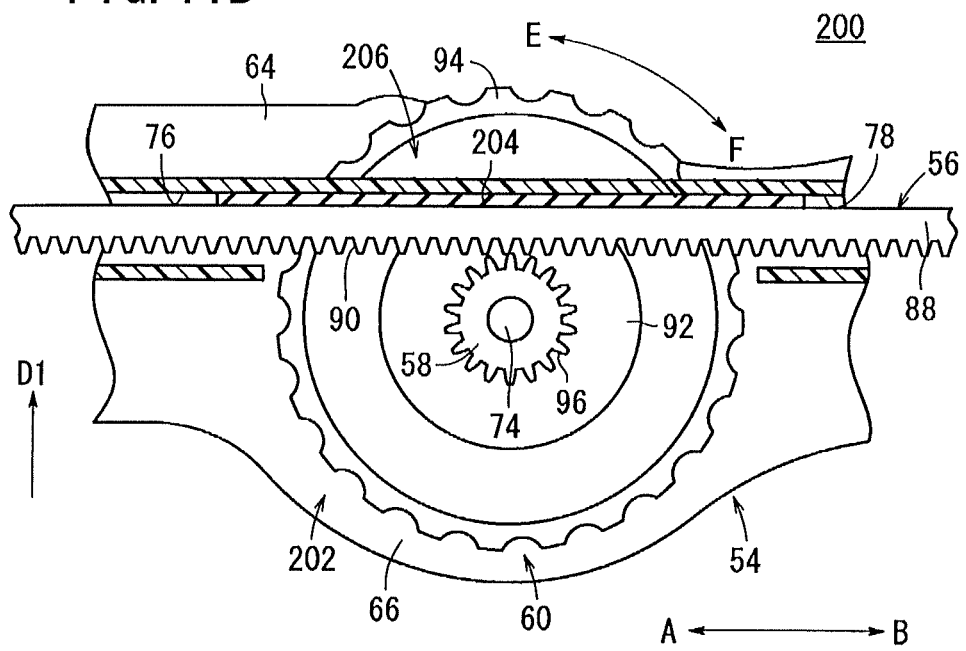
FIG. 11B is another enlarged side view showing a non-meshed state in which the rack member of FIG. 11A has been moved in a direction for spacing away from the first gear while compressing an elastic member.

As shown in FIGS. 11A and 11B, the stent delivery system 200 of the third embodiment differs from the stent delivery systems 10 and 150 of the first and second embodiments in that an elastically deformable elastic member 204 configured to be elastically deformed is disposed between the rack member 56 constituting an operating unit 202 and the inner wall surfaces of the first and second containing grooves 76 and 78 so that the rack member 56 can be moved upwardly by compressing the elastic member 204.

The elastic member 204 is formed, for example, from a rubber or the like, in a plate-like shape with a substantially uniform thickness, and has a predetermined resilient force in the thickness direction of the elastic member 204. The elastic member 204 is mounted between a top surface of the second block 88 constituting the rack member 56 and the inner wall surfaces of the first and second containing grooves 76 and 78.

In the stent delivery system 200 having the elastic member 204 as described above, in the case where movement of the outer tube body 14 and the rack member 56 in the axial direction becomes difficult for some reason and the operator continues to forcibly rotate the rotary roller 60, a load G of not less than a predetermined value is exerted on the rotary roller 60 radially outward (in the direction of arrow C1) and upward (in the direction of arrow D1) due to the rotation of the rotary roller 60, as shown in FIG. 11B.

In the third embodiment, also, the load G is set on the basis of a lowest-yield-point component of such components as the outer tube body 14, the inner tube body 12, the operating unit 202, etc. constituting the stent delivery system 200. Then, the second tooth portion 96 of the first gear 58 runs onto the first tooth portion 90 of the rack member 56 (i.e., the second tooth portion 96 becomes separated from or moves out of meshing engagement with the first tooth portion 90), of which movement is restricted, and the rack member 56 is pressed upward (in the direction of arrow D1) so as to push against the resilient force of the elastic member 204. The pushing of the rack member 56 results in a non-meshed state in which meshing between the first gear 58 and the rack member 56 has been released, so that transmission of the rotating force of the rotary roller 60 to the rack member 56 is avoided.

Thus, the rack member 56 is provided in the housing 54 in the state of being movable upward (in the direction of arrow D1) through the elastic member 204, and the elastic member 204 and the rack member 56 function as a releasing mechanism 206 by which the meshed state of the rotary roller 60 and the rack member 56 constituting the operating unit 202 are released. The elastic member 204 is thus a resilient deformable member that allows the meshing engagement between the teeth 96 on the rotary roller 60 (gear 58) and the teeth 90 on the rack member 56 to be released when a load G of not less than a predetermined value is exerted on the rotary roller 60 as described above.

In the third embodiment, the rack member 56 is so provided as to be freely movable in the direction for being spaced away from the first gear 58 of the rotary roller 60 (in the direction of arrow D1) relative to the housing 54. This helps ensure that, when a load G of not less than a predetermined value is exerted on the rotary roller 60 radially outward (in the direction of arrow C1) and upward (in the direction of arrow D1), the rack member 56 is moved in the direction for spacing the teeth 90 away from the first gear 58 (in the direction of arrow D1) against the resilient force of the elastic member 204 disposed on the upper side of the rack member 56, and the meshing engagement between the rotary roller 60 and the rack member 56 is released.

As a result, even in the case where the operator continues to forcibly rotate the rotary roller 60, the rack member 56 is prevented from being forcibly pulled due to the rotation of the rotary roller 60. Therefore, breakage of the lowest-yield-point component in the stent delivery system 200 can be rather securely prevented. Accordingly, a situation in which a broken component of the stent delivery system 200 is left in a lumen of a living body can be avoided.

The detailed description above describes embodiments of a stent delivery system disclosed by way of example. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A stent delivery system comprising:
   an inner tube;
   a stent possessing a center axis, the stent being compressed toward the center axis and being disposed on a distal-side outer surface of the inner tube during insertion of the stent into a lumen of a living body, the stent being restorable into its pre-compression shape by expanding outwardly when indwelled in the lumen of the living body;
   an outer tube disposed on an outer surface side of the inner tube and possessing a lumen containing the stent, the outer tube permitting release of the stent to exterior of the stent deliver system by axially and proximally moving the outer tube relative to the inner tube; and
   an operating unit for axially moving the outer tube relative to the inner tube;
   the operating unit comprising:
     a housing;
     a rotary body rotatably supported relative to the housing so that the rotary body is rotatable relative to the housing, the rotary body possessing a first tooth portion;
     a rack body axially movable relative to the housing so that the rack body is movable relative to the housing in an axial direction, the rack body possessing a second tooth portion in meshing engagement with the first tooth portion, the rack body being connected to the outer tube so that the rack body and the outer tube move together in the axial direction; and
   a releasing mechanism by which the meshing engagement between the rotary body and the rack body is released when a load of not less than a predetermined value is exerted on either one of the rotary body and the rack body, the releasing mechanism moving either one of the rotary body and the rack body in a direction orthogonal to the axial direction.

2. The stent delivery system according to claim 1, wherein load is equal to or less than a yield point of a member having a lowest yield point, the member being one of the inner tube, the outer tube and the operating unit.

3. The stent delivery system according to claim 1, wherein the releasing mechanism includes a resilient member in the housing which biases the rotary body toward the rack body.

4. The stent delivery system according to claim 1, wherein the releasing mechanism includes a plurality of springs positioned in the housing and biasing the rotary body toward the rack body.

5. The stent delivery system according to claim 1, further comprising a curved wall positioned in the housing, and wherein the releasing mechanism includes a support body positioned in the housing and a plurality of springs positioned in the housing between the curved wall and the support body.

6. The stent delivery system according to claim 1, wherein the releasing mechanism includes the rack body which has an inner cavity therein and which is bendable in a direction for spacing away from the rotary body.

7. The stent delivery system according to claim 1, wherein the releasing mechanism includes an elastic body disposed between the housing and the rack body and applying a resilient force biasing the rack body toward the rotary body.

8. A stent delivery system comprising:
   an inner tube possessing a lumen and open opposite ends communicating with the lumen of the inner tube, the inner tube possessing an outer surface;

an outer tube possessing an inner surface and surrounding the inner tube so that a space exists between the inner surface of the outer tube and the outer surface of the inner tube, the outer tube being axially movable relative to the inner tube;

a stent positioned in the space between the inner surface of the outer tube and the outer surface of the inner tube, the stent being compressed radially inwardly and disposed in surrounding relation to the inner tube, and being expandable radially outwardly to be indwelled in a lumen of a living body when the outer tube is axially moved relative to the inner tube to expose the stent to exterior of the outer tube; and an operating unit for axially moving the outer tube relative to the inner tube;

the operating unit comprising:
- a housing possessing an interior in which is positioned the inner tube and the outer tube;
- a rotary body rotatably supported on the housing so that the rotary body is manually rotatable relative to the housing, the rotary body possessing an outwardly projecting first tooth portion;
- an axially movable second tooth portion in meshing engagement with the first tooth portion so that rotation of the rotary body results in axial movement of the second tooth portion, the second tooth portion being connected to the outer tube so that axial movement of the second tooth portion resulting from rotation of the rotary body results in axial movement of the outer tube; and
- a resilient deformable member which is positioned in the housing in operative association with either the rotary body or the second tooth portion and which is deformed when a load of not less than a predetermined value is exerted on the rotary body so that the first tooth portion and the second tooth portion move out of meshing engagement with one another to prevent rotation of the rotary body from being transferred to the second tooth portion by way of the first tooth portion, the resilient deformable member including a spring in the housing which biases the rotary body toward the second tooth portion.

9. The stent delivery system according to claim 8, wherein the second tooth portion is provided on a rack body, and wherein the resilient deformable member includes a plurality of springs positioned in the housing and biasing the rotary body toward the rack body.

10. The stent delivery system according to claim 8, further comprising a curved wall positioned in the housing, and wherein the resilient deformable member includes a support body positioned in the housing and a plurality of springs positioned in the housing between the curved wall and the support body.

11. The stent delivery system according to claim 8, wherein the second tooth portion is provided on a rack body, the deformable member including the rack body being provided with an inner cavity so that the rack body is bendable in a direction spacing the second teeth away from the first tooth portion of the rotary body.

12. The stent delivery system according to claim 8, wherein the second tooth portion is provided on a rack body, the deformable member including an elastic body disposed between the housing and the rack body and possessing a resilient force biasing the rack body toward the rotary body.

* * * * *